(12) United States Patent
Terry

(10) Patent No.: US 12,357,877 B2
(45) Date of Patent: Jul. 15, 2025

(54) USING WEARABLE DEVICE DATA TO ENABLE CONTROL OF AN APPLICATION

(71) Applicant: ProActive Health IP, LLC, Saratoga Springs, UT (US)

(72) Inventor: Joshua Stewart Terry, Saratoga Springs, UT (US)

(73) Assignee: Proactive Health IP, LLC, Saratoga Springs, UT (US)

( * ) Notice: Subject to any disclaimer, the term of this patent is extended or adjusted under 35 U.S.C. 154(b) by 353 days.

(21) Appl. No.: 18/088,914

(22) Filed: Dec. 27, 2022

(65) Prior Publication Data

US 2023/0201662 A1  Jun. 29, 2023

Related U.S. Application Data

(60) Provisional application No. 63/293,997, filed on Dec. 27, 2021.

(51) Int. Cl.
A63B 24/00 (2006.01)

(52) U.S. Cl.
CPC ...... *A63B 24/0059* (2013.01); *A63B 24/0062* (2013.01); *A63B 2220/836* (2013.01)

(58) Field of Classification Search
CPC ............ A63B 24/0059; A63B 24/0062; A63B 2220/836; G06Q 20/32; G06Q 30/0207; G06Q 30/0209; G06Q 30/0226; G07F 17/3244; G16H 40/63; G16H 40/67; G16H 50/30
USPC .......................................................... 700/91
See application file for complete search history.

(56) References Cited

U.S. PATENT DOCUMENTS

| 10,265,624 | B2 | 4/2019 | Bhogal et al. |
| 10,467,716 | B2 | 11/2019 | Hoffman et al. |
| 10,776,739 | B2 | 9/2020 | Blahnik |
| 11,298,062 | B2 * | 4/2022 | Ellison ................. G16H 50/20 |
| 11,610,691 | B2 * | 3/2023 | Damani ............... G16H 40/67 |

(Continued)

FOREIGN PATENT DOCUMENTS

| WO | 2010024533 A2 | 3/2010 |
| WO | 2018151749 A1 | 8/2018 |

OTHER PUBLICATIONS

"HeroFit The Fitness Game"; https://herofitgame.com/; obtained from the HEROFIT website on Mar. 29, 2022; 2 pages.

*Primary Examiner* — Pierre E Elisca
(74) *Attorney, Agent, or Firm* — Workman Nydegger

(57) ABSTRACT

Techniques for rewarding users based primarily on performance scores as obtained during play of an application and based secondarily on health metric data ("HMD") obtained from performing exercise are disclosed. A baseline or minimum exercise requirement is established, where this requirement is generally achievable regardless of one's initial health status. Satisfaction of that baseline exercise requirement then unlocks a user's ability to engage with an application, which generally challenges the user's non-physical abilities. The user's performance in that application is then the deciding factor as to who wins a reward program. Because the exercise aspect is designed to be generally achievable for most if not all users, those users are now equally encouraged or incentivized to participate in the exercise reward program because the determination of who will win is now separated from a user's health status.

20 Claims, 11 Drawing Sheets

(56) References Cited

U.S. PATENT DOCUMENTS

2010/0125028 A1    5/2010  Heppert
2016/0346607 A1   12/2016  Rapfogel
2020/0253527 A1*  8/2020  Ellison .................. A61B 5/165

* cited by examiner

USING WEARABLE DEVICE DATA TO ENABLE CONTROL OF AN APPLICATION

CROSS-REFERENCE TO RELATED APPLICATIONS

This application claims the benefit of and priority to U.S. Provisional Patent Application Ser. No. 63/293,997 filed on Dec. 27, 2021, and entitled "Using Wearable Device Data To Enable Control of an Application," and which application is expressly incorporated herein by reference in its entirety.

FIELD

The present disclosure relates generally to reward systems, methods, and computer-readable media for providing rewards, and more particularly, to rewarding a user based on the user's engagement with an application, where the ability to unlock or use the application is based on the user's health metric data.

BACKGROUND

The popularity of health-related devices has expanded significantly in the past few decades, especially with the increasing cost of healthcare. Indeed, the healthcare industry has been trying to find ways to incentivize individuals to live a healthier and more active lifestyle. One way the healthcare industry has been trying to get individuals to live healthier is by promoting the use of a step counter.

A step counter is a device designed to count the number of steps a user walks within a given time period (e.g., often a single day). Step counters are used to encourage people to set daily/monthly physical activity goals and to possibly even receive rewards based on their step performance. Likewise, a pulsometer, blood pressure monitor, or any other device, which can optionally be incorporated into a smartwatch or a smartphone, are used to monitor health conditions of users and to encourage the users to set goals and to regularly exercise.

Sensor data acquired from a wearable health tracking device can be consumed and processed. This data can be analyzed to determine how active a person is. Although there are countless ways in which the acquired data can be processed, there is still a significant need to improve how that data is used, particularly in the context of reward programs.

Reward programs are designed to encourage people to engage in exercise and to set exercise goals, as determined by the user's health metrics (e.g., steps walked). One of the primary purposes of a reward program is to try to particularly incentivize those individuals who typically do not lead an active lifestyle. Stated differently, one goal of a reward program is to try to get less-healthy people more healthy, via engagement with the program.

Unfortunately, it is often the case that the top performers of the reward program (i.e. those who typically win) are individuals who already engage in an active lifestyle. Those top performers are often the individuals who win the program and thus receive the reward. The result of such a scenario is that less active individuals are left with little-to-no incentive to participate because they know beforehand that the hyper-active or ultra-healthy participants will almost always win.

Thus, it is often the case that the primary purpose of a reward program (i.e. to get less healthy people to participate and to become healthier) is often defeated or at least mitigated because those less healthy people often feel immediately defeated when they know that highly active individuals are also participating in the program. Stated differently, conventional exercise reward programs actually adversely impact or incentivize the majority of users (particularly the less healthy users) in a way that they are not encouraged but rather are discouraged to set goals because they know beforehand that they are not going to be rewarded. What is needed, therefore, is an improved technique for "leveling the playing field" so that all participants, regardless of their initial health status, are provided an equal opportunity to potentially win an exercise reward program.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

The present disclosure relates to reward systems, methods, and computer-readable storage devices for rewarding users based primarily on performance scores as obtained during play of an application and based secondarily on health metric data ("HMD") obtained from performing exercise. The disclosed embodiments initially establish a baseline or minimum exercise requirement, or rather an exercise requirement that is achievable regardless of one's initial health status. Satisfaction of that baseline exercise requirement then unlocks the user's ability to engage with an application, which can be designed to challenge various non-physical abilities of the user. The user's performance in that application is then the deciding factor as to who wins the reward program. Because the initial exercise aspect is designed to be generally achievable for most if not all users, those users are now equally encouraged or incentivized to participate in the exercise reward program because the determination of who will win is now de-linked or separated from a user's health status.

Stated differently, although the initial exercise unlocks the ability to play an application, it is the play of the application that will determine who will win the reward program. Thus, the disclosed embodiments separate the exercise aspect from the prospects of winning the reward program. By rewarding users based on performance scores in an application (not based on exercise), users with normal or low health conditions may be able to receive rewards by winning the program, whereas previously the winners were almost always the most healthy individuals.

Accordingly, as described herein, a reward system provides a reward primarily based on usage of an application and secondarily based on health metrics data. The reward system includes one or more processors and one or more computer-readable hardware storage devices that store instructions. When the processor executes the instructions, the reward system acquires, during a unit period, health metric data from a health tracking device. The health metric data includes physical activity data and/or physiological data. The embodiments convert the health metric data into one or more application tokens, which provide access to an application. The user can then use the tokens to engage with the application. That is, the embodiments provide access to the application when the number of tokens is greater than or equal to a first threshold. During this engagement, the embodiments acquire (e.g., from the application) one or more points that are based on usage of the application. The embodiments facilitate access to a reward when the points are greater than or equal to a second threshold.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Figure 1:
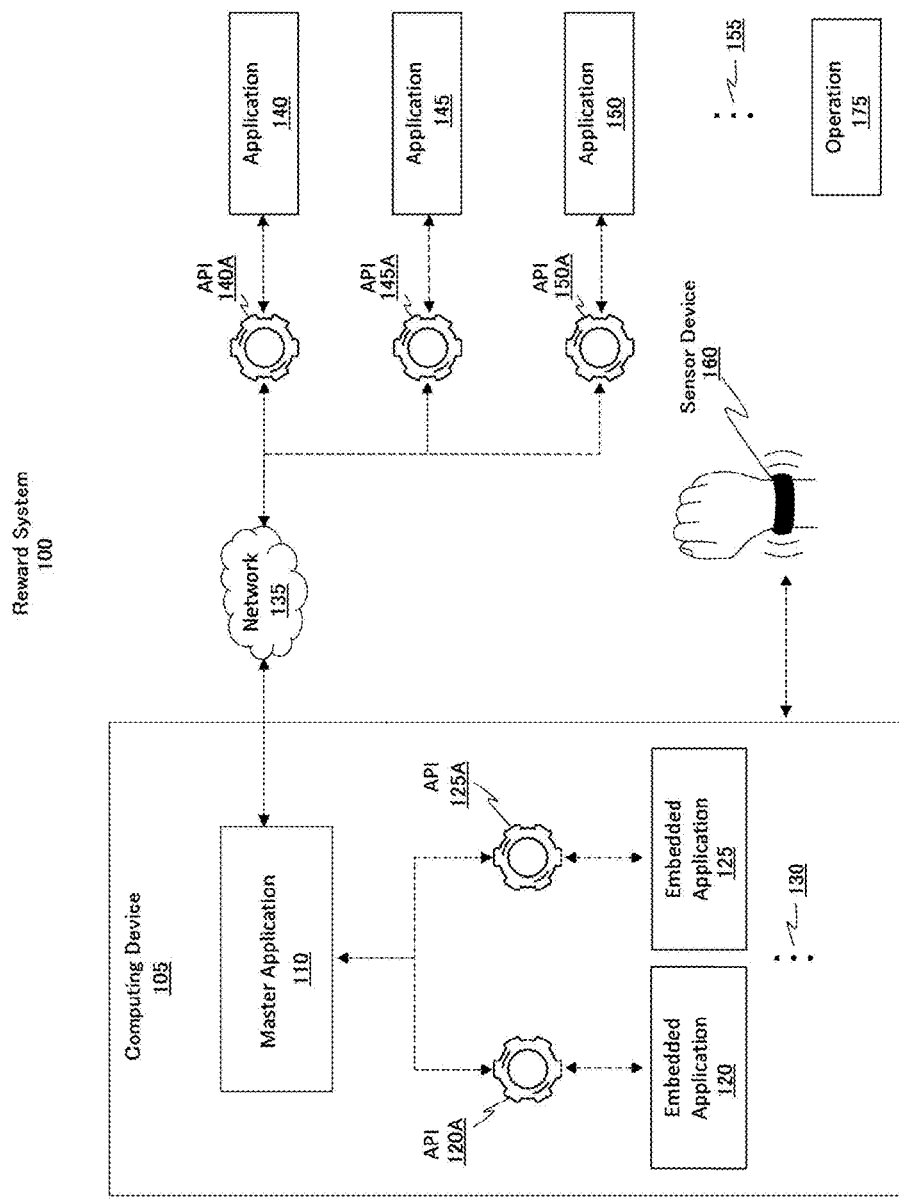
FIG. 1 illustrates a graphical diagram for a reward system, which enables users to play applications based on health metric data and which provides rewards to the users based on performance scores achieved from playing the applications.

Embodiments disclosed herein relate to reward systems, devices, and methods for enabling users to play applications based on health-related or health metric data (HMD) and to receive rewards based on performance with respect to the applications. Stated another way, the embodiments relate to various techniques for providing access to a reward based on a user's performance in engaging with an application, where the user's access to engage with the application is determined based on the user's health metric data. As a consequence, the ability to obtain the reward is primarily based on the user's performance in engaging with the application and is not primarily based on the user's health metric data.

Health metric data is acquired, during a unit period (e.g., perhaps a day) from one or more sensors and converted into one or more application tokens. Users are eligible to play an application when they achieve or reach a minimum health metric requirement, which is designed to be achievable for a large majority of users, if not all. The health metric data is then converted to one or more tokens that enable usage of an application. The user then uses the tokens to engage with the application. The user's performance in the application will then determine his/her status with regard to the reward system.

In this manner, the ability to engage with the application is unlocked by performing a minimum level of exercise or activity. Once the application is unlocked, then the user can attempt to reach a highest score in the application. Typically, engagement with the application involves non-strenuous or non-physical activity. The user's score can then be compared to other users' scores to determine who will win the reward program. Thus, the determination of who will win the reward program is primarily based on the user's performance in the application (often non-physical performance) and secondarily based on the user's exercise abilities. The user's health metrics enable the user to engage with the application, and the user's engagement with the application is the determining factor in deciding who wins the exercise reward program. Thus, the user's health metrics contribute to the user's potential for success in a "secondary" manner (e.g., by enabling engagement with the application) while the user's performance in the application contributes to the user's potential for success in a "primary" manner.

Notably, the application tokens are used to determine the user's eligibility to engage with the applications; those tokens are not used to actually reward the users. Thus, the tokens are distinct from any points or score that is obtained from engaging with the application. Instead, the user's engagement with the application determines his/her potential to win the exercise program reward. The application tokens thus motivate all users, regardless of their health state, to set physical/health goals and to exercise. The application tokens are designed to be readily achievable, and those tokens can be used to engage with the application. The user's performance in the game/application is the determining factor for deciding who will win the exercise reward program. Thus, all users, regardless of their physical state, are provided opportunities to win the reward program. Previously, it was typically the case that only very healthy individuals ever won the reward program.

Further, after receiving the application tokens, users can play applications individually or in a group. Rewards will be given to individual users or groups of users based on the performance of the applications. Since the application tokens provide a set number of tries to engage with the applications, the users are generally motivated to exercise so as to achieve another application token. Thus, by basing the application tokens on health metric data and by basing actual rewards on how the user performs in an application, a majority of users are motivated and encouraged to exercise.

Notably, the minimum health metric requirement is one that will still be challenging while also being one that can be achievable by the general population. That is, the minimum requirement is achievable by all who are willing to make a reasonable effort, which is a level of effort that is sufficient so as to be beneficial to a person's health. Optionally, the winner of the exercise program can also be selected via a raffle in which qualifying participants (e.g., those who completed the program or those whose scores were above a threshold) are included. In some cases, the top scorer can be selected as the winner.

Examples of Technical Benefits and Advantages

The following section outlines some example improvements and practical applications provided by the disclosed embodiments. It will be appreciated, however, that these are just examples only and that the embodiments are not limited to only these improvements.

The disclosed embodiments bring about numerous benefits to how applications are controlled as well as to the health and well-being of users of those applications. Specifically, the embodiments track health metric data of a user, such as perhaps the number of steps the user takes, the number of heartbeats the user has, the amount of time the user is at the gym, or perhaps even the amount of time the user is in an outdoor environment. These metrics are then converted into application tokens. These application tokens can be designed to control any type of application and can be designed to exert any type of control over that application.

As a user acquires more application tokens (e.g., by reaching his/her daily health metric baseline), the user will be provided more or additional opportunities to use and interact with the application. In some cases, the use of the application tokens can be considered as an incentive program to incentivize the user in leading a healthier lifestyle, such as by walking more, exercising more, or even spending more time outdoors. More application tokens will be provided to those who engage in healthy lifestyles. Competition between users can also be facilitated via the disclosed principles.

In contrast with traditional exercise reward programs, the embodiments are designed to disassociate the ability to win the reward program from the user's exercise regime. That is, the embodiments establish a baseline set of exercise metric standards, which are designed to be achievable by a large majority (if not all) users. Achieving these standards allows a user to obtain application tokens. The tokens, as indicated above, enable the user to engage with an application. Notably, the user's performance within that application is now the controlling or deciding factor in who will ultimately win the exercise reward program. In this manner, there is an initial physical aspect to the challenge, but the ultimate factor in deciding who will win is primarily a non-physical aspect. By configuring the embodiments in this manner, all users, regardless of their physical state, are now essentially provided an equal footing or an equal playing field with regard to the possibility of winning the exercise reward program.

The embodiments not only promote healthy physical activity, but they can also be used to promote healthy mental and emotional responses in users. For instance, studies are being conducted documenting the impact of social media on users, particularly for signs of depression or social anxiety. By following the principles discussed herein, access or use of a particular social media platform can be controlled or limited based on how active a lifestyle the user has. If the user is less active during a particular day, then the application can be controlled in a manner so as to limit the amount of time the user can use a given application.

In this sense, the embodiments are designed to promote healthy lifestyle choices. In addition to those benefits, some (though not all) of the disclosed embodiments are designed in a manner to enable a master application to control the operations of a child application based on acquired health tracking metrics. The master application can acquire the health metrics and then convert those metrics into application tokens. In some cases, these application tokens can be delivered to a child application via one or more application programming interfaces (API)s. The operations of the child application can then be internally governed or controlled, at least in part, by the application tokens, which can be generated over time as a user builds up his/her health metrics. In some cases, the master application is able to exert external control over the application, such as via various operating system commands (e.g., hiding a visibility of the application, forcefully closing an application, etc.). In this sense, the embodiments provide a real-world and practical scenario in which applications are governed and controlled in a specified manner to achieve a desired outcome. Accordingly, these and numerous other benefits will now be described in detail throughout the remaining portions of this disclosure.

Example Systems and Architectures

FIG. 1 illustrates a reward system 100 for providing rewards to users according to embodiments of the present disclosure. The reward system 100 may include a computing device 105, which can be any type of device, such as a smartphone, tablet, laptop, and the like. The computing device 105 may execute or host a master application 110, which manages any applications related to rewarding users with points or a score. The master application 110 may interact with any number or type of other applications, such as embedded applications 120 and 125, which are a type of sub-application that is integrated therein as a part of the master application 110. By "embedded," it is generally meant that the embedded applications 120 and 125 do not operate independently of the master application 110 and that the embedded applications 120 and 125 are available only when the master application 110 initiates them.

In addition to the embedded applications 120 and 125 or locally-executing applications, the master application 110 may also communicate over a network 135 with any number of externally-executing applications, such as applications 140, 145, and 150. The ellipsis 155 indicates that any number of applications may be included in this externally-executing application group.

Each application may be associated with its own respective API. For instance, application 120 is associated with application programming interface ("API") 120A, application 125 is associated with API 125A, application 140 is associated with API 140A, application 145 is associated with API 145A, and application 150 is associated with API 150A. Generally, an "API" is an intermediary software entity that enables two applications to communicate with one another and to send and receive data. In this sense, the master application 110 may use the respective APIs to communicate with the various different applications. The applications may be games for the user to play, social media, or skill training programs for the user. For example, the game may be a racecar game, Halo, Minecraft, roulette, card game, a strategic game, or any other type of game or application. The social media may include Facebook®, Twitter®, Snapchat®, Instagram®, and so on. In a case where a company wants its employees to learn a set of skills, the applications may be the corresponding skill training programs (e.g., word processor, spreadsheet, presentation, database, database search engine, programing language, MTLAB, etc.).

The reward system 100 may include or may communicate with a sensor device 160 that is in communication with the computing device 105 and in particular with the master application 110. The sensor device 160 generates sensor data based on an activity of the user or a physiological response of the user. The sensor device 160 may be an activity tracking device (e.g., a pedometer) or physiological tracking device (e.g., a pulsometer or blood pressure monitor). The master application 110 acquires the sensor data or health metric data (i.e. the health tracking activity or physiological data) from the sensor device 160.

Any number of different communication channels or protocols may be used, such as Bluetooth, near field communication (NFC), or any other wireless connection. In some cases, a wired connection may also be used. In some cases, the computing device 105 may be a smartphone or smart device and may be considered as the sensor device 160. That is, in some scenarios, the computing device 105 may document and record a user's activity and/or physiological response in a form of health metric data.

In some cases, the sensor device 160 may be an integral part of the computing device 105 itself and may not be a separate device. For instance, the computing device 105 might be a smartphone having GPS capabilities. The GPS may be used to track movements of the user, and these movements may be considered the user's activity. The computing device 105 might include a heart tracking sensor or even a step counter. Any type of sensor can optionally be included in the computing device 105 to track the user's health metrics. Accordingly, the sensor device 160 does not necessarily have to be a separate device relative to the computing device 105.

In some embodiments, health metric data may be acquired from a separate health tracking device, which may be a wearable sensor, smart sensor, or legacy sensor. The health metric data contains data related to activities and/or physiological responses of users, and the activities and/or responses are recorded in a form of health metric data in the wearable health tracking device.

The master application 110 may convert the health metrics into one or more application tokens, which are provided to enable the user to engage with a set of applications 120, 125, 140, 145, and 150. Stated differently, the application tokens may be used to control usage and/or functionality of the applications. In this manner, the user's physical activity enables the user to engage with an application.

With traditional exercise reward programs, higher exercise performers (i.e. those who have higher health metric data) would receive higher scores, leading to a higher likelihood of winning the exercise reward program. Less active individuals often recognized that they would not be able to perform as much or as well as the higher performers. Thus, it was often the case that the less active individuals would opt out of the exercise rewards program entirely, or perhaps immediately quit when they realize they cannot win, or perhaps give only a bare minimum performance (e.g., by signing into the application every day without completing the exercise requirements). The disclosed embodiments are designed to enable all participants an equal chance at winning the exercise rewards program because now the determination as to who will win is based on the user's performance with respect to non-physical activity.

In particular, a user's exercise performance grants them a number of tokens during a unit period (e.g., a day). In some embodiments, the number of tokens is limited during that unit period. For example, if a user decides to engage in additional exercise beyond the baseline exercise requirement for that day, that user will not be provided additional tokens during that day. The user will have to wait until the next unit period before additional tokens can be earned.

Notably, the exercise performance requirements are designed to be achievable by essentially all users. These tokens enable the user to engage with an application. The user's engagement with the application is primarily non-physical in nature, though some applications may task the user with performing some optional additional exercise or health promoting options. Generally, however, the interaction with the application is non-physical.

The user's engagement with that application then enables the user to achieve points. These are the points that are used to determine a user's status in the exercise rewards program. Thus, the embodiments break the link that previously existed with exercise rewards programs in which the winner of the program was the individual who exercised the most. Now, the winner of the program is the individual who performs best with regard to the applications. The ability to use those applications, however, is governed by the exercise baseline requirement.

In some implementations, the number of application tokens can be proportional to performance in health metric data up to a specified level, as discussed previously. In this manner, the same number of application tokens are given to all users who achieve a threshold performance in the health metric data. An example will be helpful.

Suppose the baseline exercise requirement is to walk 6,000 steps per day. If a user achieves this health metric, that user will be provided with a set number of application tokens. Users can elect to walk more than that minimum number of steps, but, at least in some embodiments, they will not be provided additional tokens during the pending unit period (e.g., a day). New tokens can be earned during the next unit period (e.g., the next day). For example, if the user walks over 20,000 steps in one day, that user will still receive the same number of application tokens as the user who walked 6,000 steps.

In one embodiment, the minimum threshold performance or exercise requirement may be predetermined based on current medical or health condition of each user. For example, if a user is a healthy young man, the threshold performance may be 7,000 steps a day. If a user is an old sick man, the threshold performance may be 4,000 steps a day. In this case, the threshold performance may be predetermined after the user enters his/her current medical and health conditions. Furthermore, the threshold performance in the health metric data may be adjusted after the medical and health conditions have changed.

In another embodiment, the threshold exercise performance requirement may be set to be the same for every user. In this case, the threshold exercise performance requirement may be the minimum threshold that a majority of users can easily achieve. Thus, a majority of users will be motivated and encouraged to exercise so that they can receive the same number of application tokens and have an equal opportunity of winning the reward program.

After the master application 110 receives the health metric data and converts the health metric data into one or more application tokens, the master application 110 allows the users to execute or play the applications 120, 125, 140, 145, 150 via the respective APIs and via the tokens. With the limited number of application tokens that are available each unit period, users are able to play the applications a limited number of times each unit period. That is, when a token is consumed by an application, the user is provided a limited number of times (or duration) to engage with that application. For example, if a user can play one application three times with one application token, after the user plays the application three times, one application token will be consumed or reduced from the user's application tokens.

In a case where the users are allowed to play the embedded applications 120, 125, the master application 110 may perform an "internal" control over the embedded applications 120, 125 inasmuch as usages of the embedded applications 120, 125 are controlled by the master application 110. In another case where the users are allowed to play the applications 140, 145, 150, the master application 110 may perform an "external" control over the applications 140, 145, 150 as usages of the applications 140, 145, 150 are controlled via the respective APIs by the master application 110 or perhaps via an operating system (OS) command.

In one embodiment, the master application 110 can be a middleware application between the operating system (OS) of the computing device 105 and the applications 120, 125, 140, 145, 150 (hereinafter the "applications" collectively or "application" individually). Thus, the master application 110 may be able to limit the users' usage of the applications entirely as the middleware can have a limited control over the applications whether or not they are embedded. In other words, the users may not be able to use the applications without achieving the performance threshold in the health metric data or without an application token.

In another embodiment, the master application 110 may be the OS and the application tokens may be delivered to the OS within which the application is executed. Since the OS has total control over the applications, the users may not be able to even execute the applications without the application tokens.

The master application 110 collects performance data or scores of the users on the applications. Rewards can then be distributed to the users based on the performance scores. By "performance score," it is meant a score that is obtained from engaging with an application.

In one aspect, an individual user may be rewarded based on his/her performance score as accrued during engagement with an application. In this case, the master application 110 can optionally reward the individual user when the performance score is greater than or equal to a predetermined threshold score. For instance, the reward can be a reward given as a part of the exercise reward program. In one scenario, rewards are given to users who achieve a minimum performance score without regard to whether other users also achieved that same minimum performance score.

In another aspect, groups of users may be rewarded together based on a group performance score, which can optionally be based on the aggregation of each individual user's score. In this case, the master application 110 sums up individual performance scores for users in the same group and rewards the group when the group performance score is greater than or equal to a group threshold score.

In yet another aspect, a number of users may be competing against one another. Whoever achieves the top score may be given a reward as a part of the exercise reward program. Additional rewards can optionally be provided to the second, third, fourth place finishers, and so on.

The rewards may be in different forms. As some non-limiting examples, the rewards can be a set number of raffles, any type of consumer products, or perhaps even a title (e.g., champion or leader of the day, week, month, or year).

Figure 2:
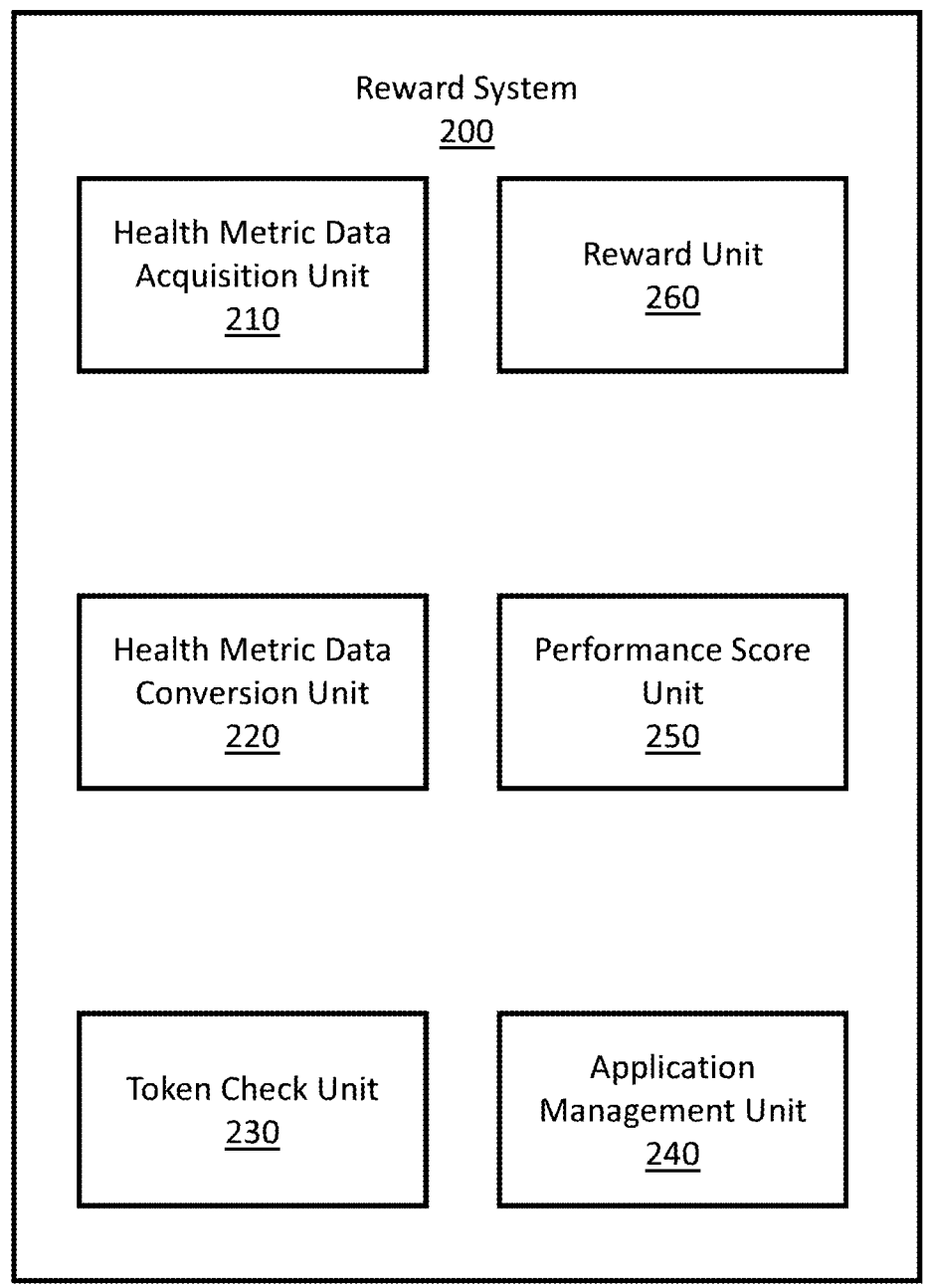
FIG. 2 illustrates a block diagram for a reward system.

FIG. 2 shows a reward system 200 according to embodiments of the present disclosure. The reward system 200 may reward users based primarily on the user's performance with respect to an application and secondarily based on health metric data. Reward system 200 of FIG. 2 is representative of the reward system 100 of FIG. 1.

Reward system 200 includes a health metric data acquisition unit 210, a health metric data conversion unit 220, a token check unit 230, an application management unit 240, a performance score unit 250, and a reward unit 260. The health metric data acquisition unit 210 communicates with and receives health metric data from a tracking device (e.g., wearable pedometer, blood pressure sensor, temperature sensor, a smartphone, smartwatch, oximeter, pulsometer, etc.). When the health metric data is in a raw data format, the health metric data acquisition unit 210 can convert the raw health metric data into useable health metric data.

For instance, the health metric data may include steps that the user has walked, calories that the user has consumed, a distance that the user has run, swam, jogged, or cycled. The health metric data acquisition unit 210 may also acquire physiological data from the tracking device. The history of physiological data may include heart rates, blood pressure, oxygen saturation levels in blood, body temperature, respiration rate, sleeping or resting hours, and so on.

The health metric data conversion unit 220 converts the health metric data and/or the physiological data into application tokens. The health metric data and the physiological data will be collectively referred to as "HMD" hereinafter below. In one aspect, the HMD conversion unit 220 converts one type of the HMD to application tokens. For example, a predetermined threshold may be 5,000 steps a day, and the HMD conversion unit 220 converts the steps by the user to application tokens. In a different scenario, the predetermined threshold may be 2,500 calories a day, and the HMD conversion unit 220 converts the calories burned by the user to application tokens. In yet another scenario, the predetermined threshold may be "x" number of heartbeats per day or "y" hours of sleep per day. The HMD conversion unit 220 can convert these metrics to application tokens.

In another aspect, the HMD conversion unit 220 may convert two or more types of the HMD to application tokens by comparing the HMD with corresponding predetermined thresholds. For example, the predetermined thresholds may include two or more from among 5,000 steps, 2,500 calories, 1-mile distance, at least 6-hour long sleep, the maximum systolic blood pressure reaching 140 mmHg while exercising, and the respiration rate reaching 25 breaths per minute. These rates, pressure, distance, calories, and steps are provided as examples without limitation but may be any number based on personal medical and health conditions and/or general statistics.

In an embodiment, the HMD acquisition unit 210 may collect HMD for a predetermined period, which can be one day, one week, or one month. The predetermined period may be any hours or a year and be determined based on a selection. The starting time of the predetermined period may be set as passage of time or based on a starting time. For example, the starting time can start from the time when the HMD acquisition unit 210 starts collecting the HMD or from the start of the day. The HMD may be accumulated during the predetermined period and reset after the predetermined period (e.g., the unit period). For example, when the number of steps is collected, and the predetermined period is one day and starts right after midnight, the HMD acquisition unit 210 accumulates the number of steps from the pedometer during the day or receives the accumulated steps from the pedometer, and the number of steps is reset to zero after the midnight.

Figure 3:
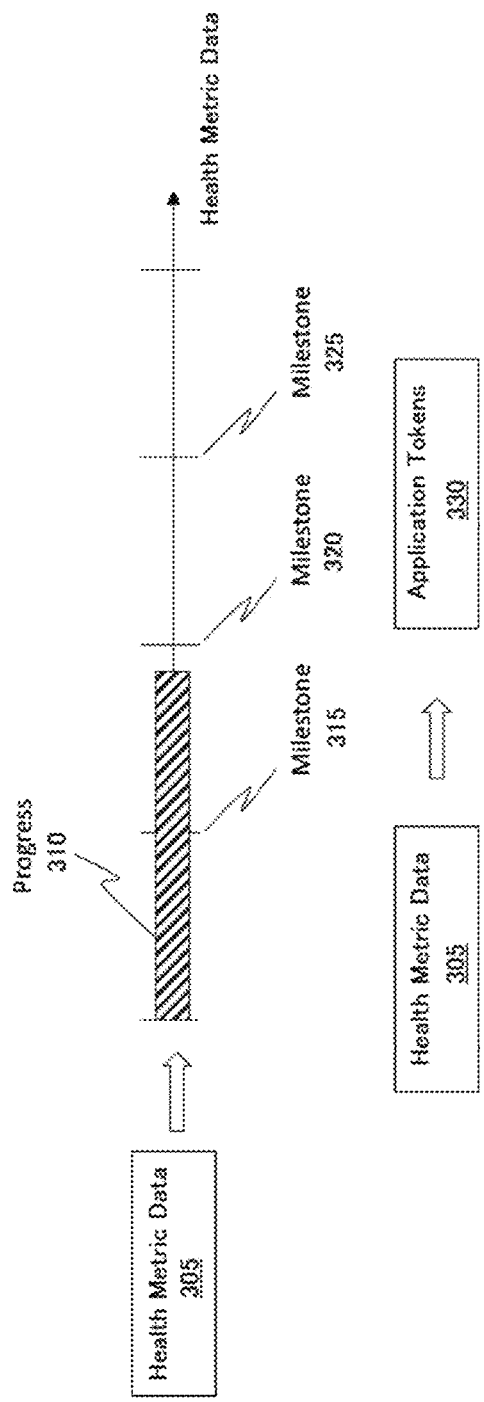
FIG. 3 illustrates a block diagram for converting health metric data to application tokens.

In embodiments, with reference to FIG. 3, application tokens are provided to users when the HMD 305 reaches a predefined stepwise milestone 315, 320, 325. The HMD conversion unit 220 receives and compares HMD 305 with several milestones 315, 320, 325. For example, the first milestone 315 may be a goal of 5,000 steps in a given day, the second milestone 320 may be a goal of 10,000 steps in a given day, and the third milestone 325 may be a goal of 15,000 steps in a given day. Currently, it might be the case that the user has walked about 8,500 steps, as shown by the progress bar 310. The number of steps is provided for explanation purposes and may include other types of health metric data 305 and may be adjusted by considering whether the milestones 315, 320, 325 can be achieved by a majority of the users. In most cases, there are a limited number of milestones. If a user continues to exercise beyond the highest milestone, that user will not be provided additional application tokens. In some limited embodiments, there might not be a cap on the milestones, and the user can optionally receive an unlimited number of tokens, though such embodiments are not preferred because such embodiments might lead to the scenario where the healthiest individuals are the only ones who end up winning the exercise program or challenge.

In some embodiments, when the HMD 305 reaches a milestone, the HMD conversion unit 220 converts the HMD 305 to a set number of application tokens (e.g., one, two, three, or more). For example, when the HMD 305 reaches the first, second, or third milestones, the HMD conversion unit 220 converts the HMD 305 to the same number of application tokens 330.

In an aspect, a timing requirement may be introduced. For example, after the HMD 305 reaches a milestone, a predetermined lapse time may have to pass. In this example, the HMD conversion unit 220 may have to check whether another milestone is reached when the predetermined lapse time has passed after the HMD 305 reached the previous milestone.

The HMD conversion unit 220 may utilize different conversion algorithms for the conversion process. In one scenario, the HMD conversion unit 220 utilizes a linear increment whenever the HMD 305 reaches a milestone. For instance, 5,000 steps may result in one application token, 10,000 steps may result in two application tokens, and 15,000 steps may result in three application tokens. On the other hand, the HMD conversion unit 220 may not convert the HMD 305 to additional application tokens after a predetermined number of application tokens has been converted. In other words, if the predetermined number of application tokens is three, any steps additional to 15,000 steps will not be converted to additional application tokens.

In another aspect, the HMD conversion unit 220 may utilize a non-linear increment or a non-linear conversion, such as a parametric equation, exponential equation, or some other algorithm. For example, 5,000 steps may result in one application token, 10,000 steps may result in two application tokens, 15,000 steps may result in four application tokens. Again, any non-linear conversion may be utilized by the HMD conversion unit 220.

The token check unit 230 checks whether the number of application tokens is greater than zero. Since the application tokens are used and reduced as a user plays an application during the predetermined period, the token check unit 230 can periodically or constantly check the user's number of available application tokens and can allow the user to access the applications when the number of remaining application tokens is greater than zero. The unit can disallow or prevent the user from accessing the applications when there is no remaining application token.

When the token check unit 230 allows a user to play an application, the application management unit 240 provides a list of applications to the user so that the user is able to play any one or more applications in the list of applications based on the remaining application tokens. The list of applications may include gaming applications, skill training applications, social media applications, or any other type of applications. In the scenario where the user plays a gaming application or a skill training application, one application token may provide a finite number of lives or chances to the user while in the gaming application. In another scenario, such as where the user runs a social media application, one application token may provide for a finite number of minutes the user can run the application. There are numerous different manners in which the application tokens may control the functionality of applications.

The application management unit 240 may add applications to or remove applications from the list. In a case where the master application of the reward system 200 is a middleware or the OS, the application management unit 240 may directly control functionality of the applications based on the application tokens.

In another case where the master application is neither a middleware nor the OS, the application management unit 240 may indirectly control functionality of the applications via the corresponding APIs based on the application tokens. In sum, the application management unit 240 directly manages embedded applications and indirectly manages external applications via APIs.

The performance score unit 250 may monitor the user's performance on the applications and update the user's performance score. In a case where each application updates the performance score by itself, the performance score unit 250 may collect performance scores from each application and calculate a total score as the user's overall performance score. In this case, each performance score may have a different weight, and the performance score unit 250 may calculate a weighted total score as the user's overall performance score.

In an aspect, the application management unit 240 may set uniform performance scores for embedded applications, thereby the user's overall performance score can be a sum of uniform performance scores of the embedded applications. In a configuration where the application management unit 240 manages external applications (e.g., applications 140, 145, 150 of FIG. 1), the performance score unit 250 may use a different weight for each external application and calculate a weighted total performance score because the scoring system of each external application is not controlled by the application management unit 240. Different weights can optionally be assigned based on the level of difficulty in engaging with an application. The weights can be defined via the exercise rewards program.

In some optional scenarios, an application may task the user with performing additional exercise feats or goals. Optionally, the performance of these additional exercises can result in the user being awarded more application tokens. In other scenarios, the performance of these additional exercises can result in the user's performance score being increased. In other scenarios, the applications may task the user with performing other goals, such as perhaps health-based goals. As one example, the user may be tasked with developing a sleep schedule, an eating regimen, or some other health-based regimen. Points can be awarded for developing the regimen. Points can also be awarded for completing the regimen.

After the user's performance score or overall performance score (hereinafter the user's performance score) and after the predetermined period (e.g., the exercise reward program can define a time period for the competition or challenge), the reward unit 260 may compare the user's performance score with a second threshold and provide a reward to users whose performance scores are greater than or equal to the second threshold. In a case where there is a group challenge, the performance score unit 250 may add performance scores of users in the same group to output a group performance score, and the reward unit 260 may reward the users in the same group whose group performance score is greater than or equal to the second threshold. The reward may be a raffle, a consumer product, money award, gift card, or a discount of health premium. Other rewards can be provided as well. In an aspect, a single user or users of a group who achieve the second threshold may receive, as a reward, a discounted medical insurance premium.

It is noted that the functionalities of all the units in the reward system 200 are performed within the predetermined period. If the predetermined period ends, all of the HMD, application tokens, and performance scores can optionally be reset to zero, and functionalities of all the units in the reward system 200 start anew. Optionally, the application tokens can persist from one predetermined period (e.g., a day) to another predetermined period within the time period established for the same exercise reward challenge. For instance, suppose a challenge is set to last 10 days. The tokens acquired during day 1, if not used during day 1, can persist to day 2, 3, 4, etc. The user can then use those tokens during subsequent days to engage with the application. Alternatively, the tokens may expire at the end of the predetermined period in which they were earned.

Example User Interfaces

Figure 4:
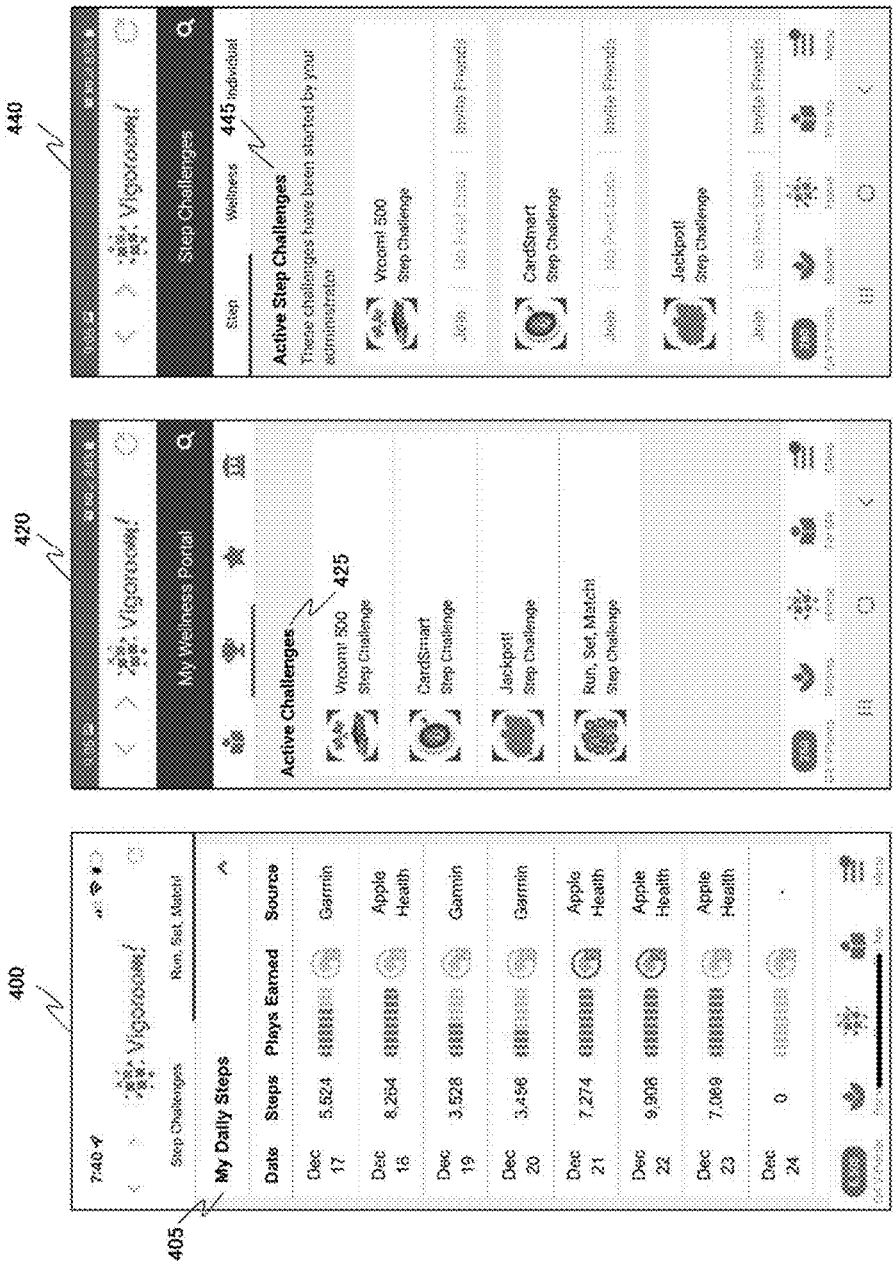
FIG. 4 illustrates user interfaces (UIs) for step challenges.
Figure 5:
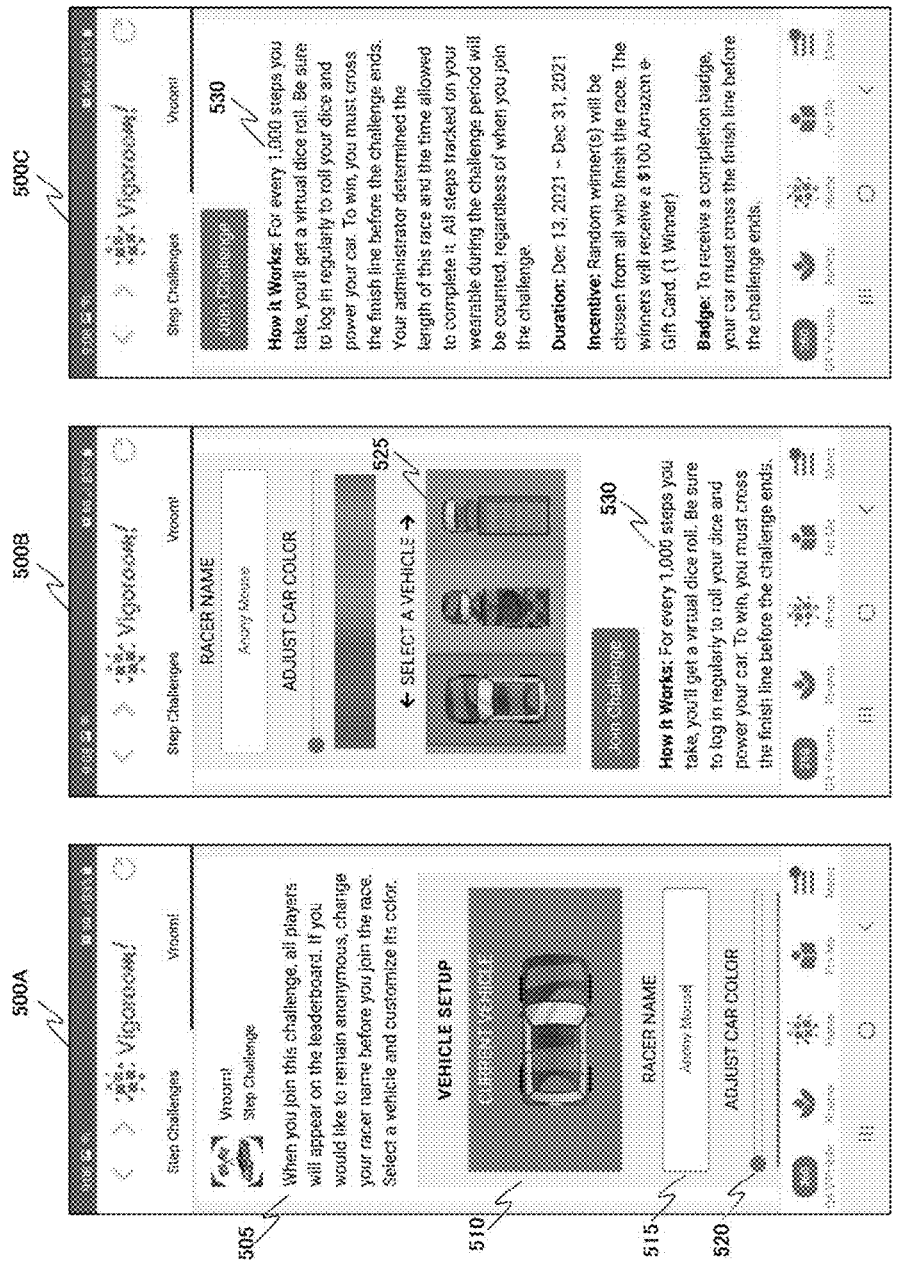
FIG. 5 illustrates UIs for a game or application challenge.
Figure 6:
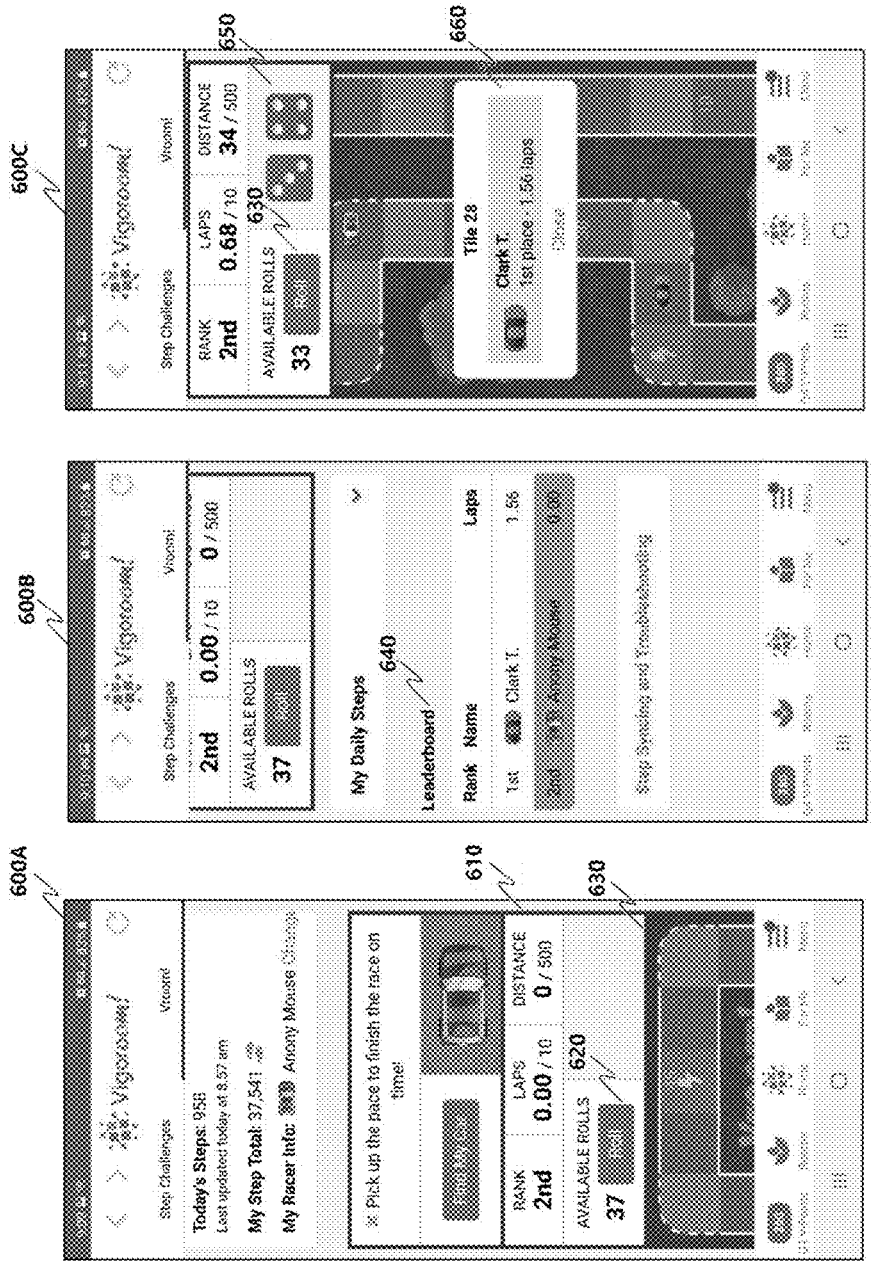
FIG. 6 illustrates additional UIs for the game challenge.
Figure 7:
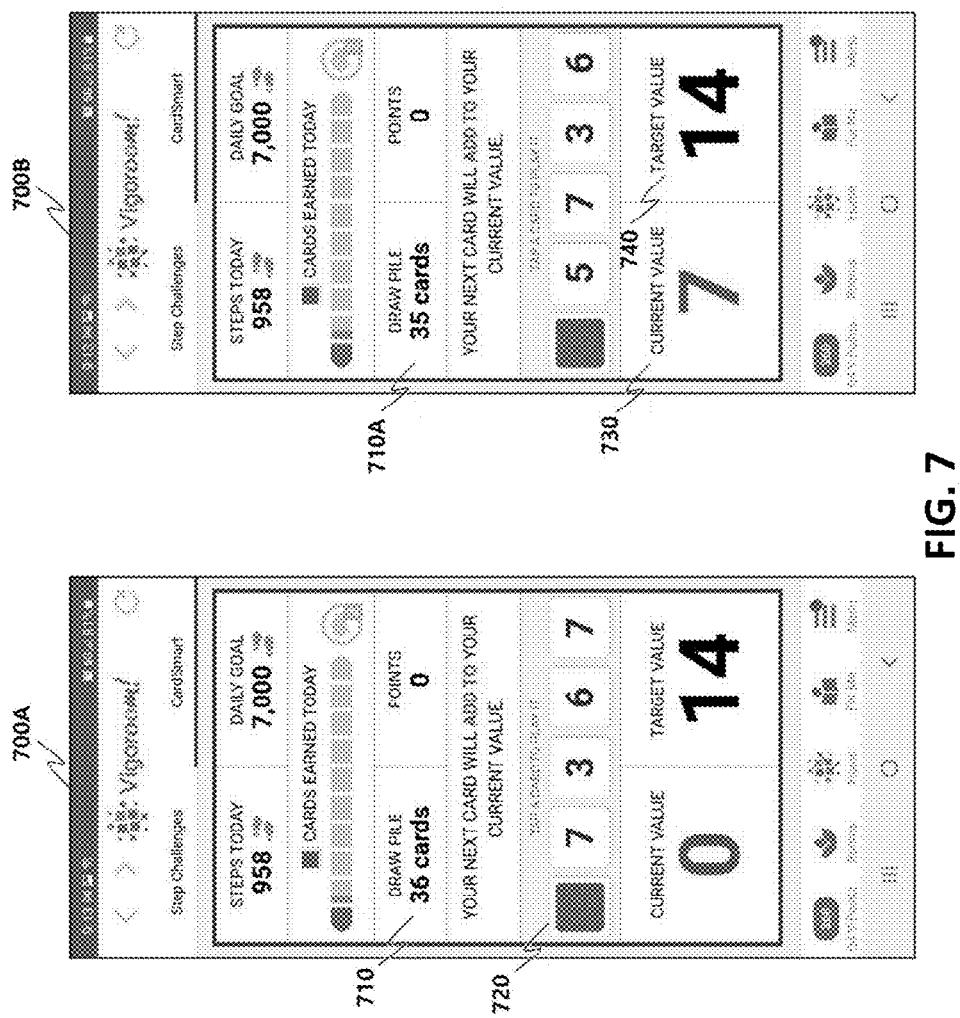
FIG. 7 illustrates additional UIs for the game challenge.
Figure 8:
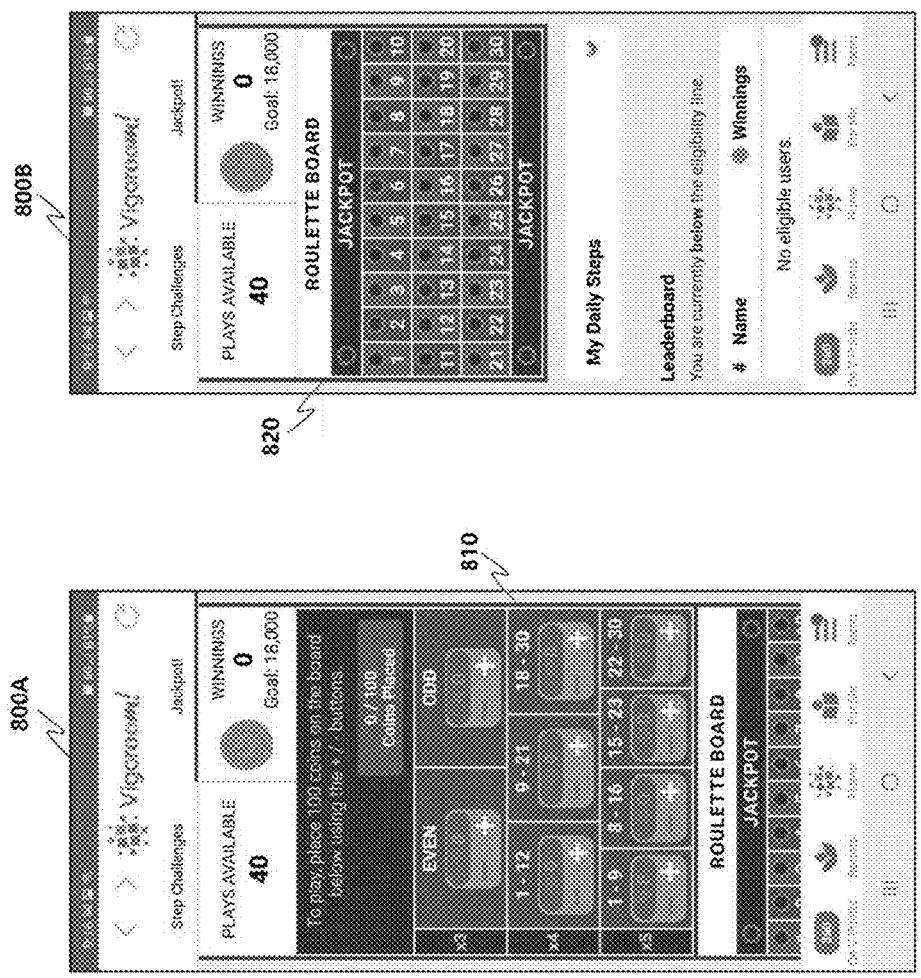
FIG. 8 illustrates additional UIs for the game challenge.
Figure 9:
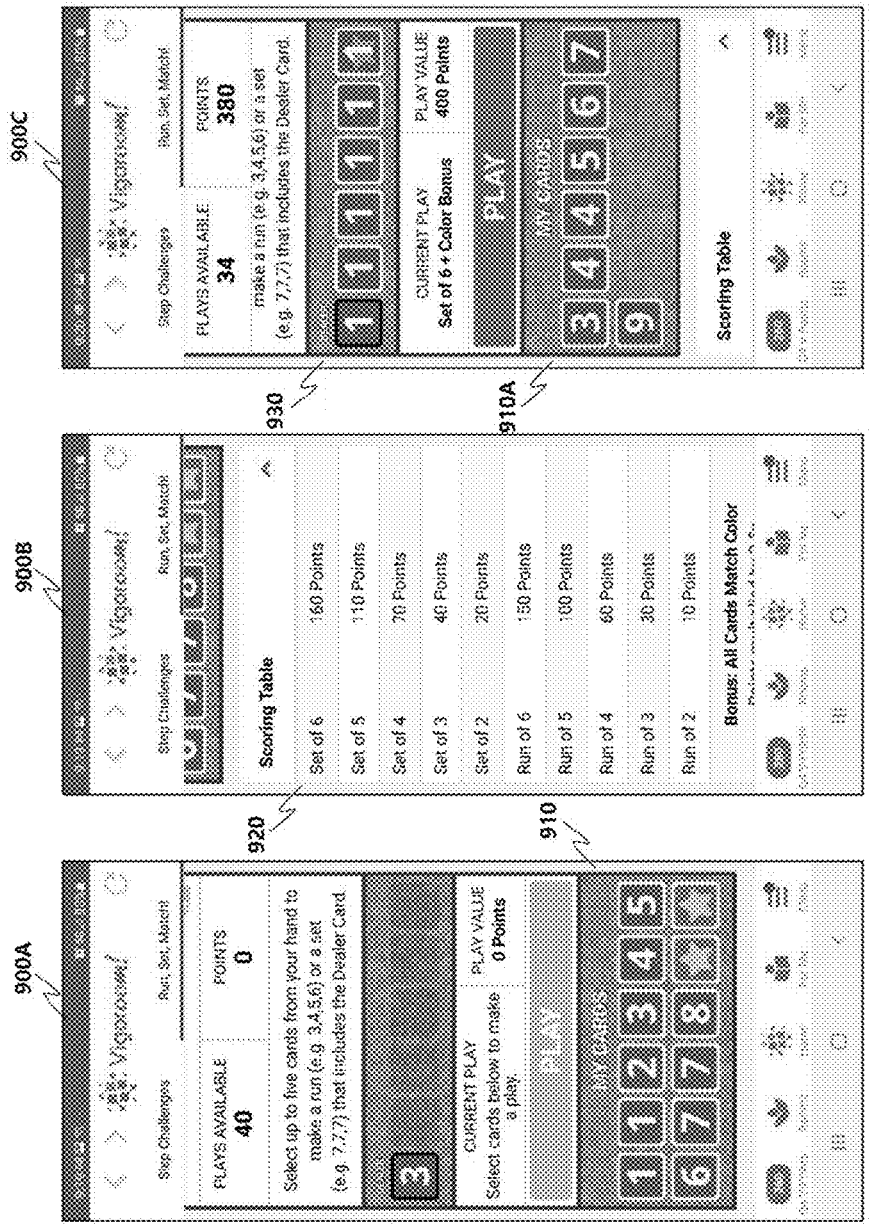
FIG. 9 illustrates additional UIs for the game challenge.

FIGS. 4-9 illustrate various different user interfaces (UIs) for different aspects or challenges according to embodiments of the present disclosure. In particular, step challenges are shown in FIG. 4, racecar challenges are shown in FIGS. 5 and 6, card game challenges are shown in FIG. 7, roulette challenges are shown in FIG. 8, and card challenges are shown in FIG. 9. The UIs of FIGS. 4-9 show how HMD can be used for game challenges in a form of screenshots of a mobile phone.

UI 400 shows daily steps window 405 of a user based on the date order. For example, on December 17, the user walked 5,524 steps and a Garmin device counted the steps. Further, based on the steps, the user earned approximately 70% of the total number of available tokens for that day, meaning that 70% of the maximum number of plays in applications (e.g., the applications 120, 125, 10, 145, 150 of FIG. 1) were obtained from the steps.

As shown in the daily steps window 405, the steps can be obtained from various sources including but not limited to the Garmin device and Apple device. Further as shown, the earned plays will be the same when the number of steps is greater than or equal to, for example, 7,000. For instance, if the baseline requirement for a single day was 7,000 steps to earn 5 tokens, the user earned 5 tokens on December 18, 21, 22, and 23. Despite the user walking more than 7,000 steps on those days, the user received only the five tokens. On days the user did not reach 7,000, the number of tokens can be prorated based on the percentage achieved or perhaps based on defined milestones, as described earlier.

UI 420 shows various active challenges 425 (e.g., exercise reward programs). As shown in the UI 420, there are gaming applications including a racecar gaming application "Vroom!500," a card gaming application "CardSmart," a game of chance gaming application "Jackpot!," and a gaming application of chance "Run, Set, Match!". These applications can be played using application tokens, which are obtained based on a user's accumulated number of steps. When a user clicks one of the gaming applications, the clicked gaming application is expanded to show menus so that the user can join the game, show stats, and invite friends as shown in UI 440. The icon labeled 445 shows another scenario illustrating the different active step challenges (e.g., exercise reward programs).

The racecar gaming application is one example of an "application" that can be engaged with to enable a user to acquire points. Of course, as described throughout this disclosure, other types of applications can also be used to acquire points.

The racecar gaming application is shown in UIs 500A, 500B, and 500C. The UI 500B is shown when a user scrolls down the UI 500A, and likewise, the UI 500C is shown when the user further scrolls down the UI 500A or scrolls down the UI 500B. As described in a description section 505, all players will appear on a leaderboard. The players can be human players or a combination of human and computer-generated players.

A user may select a vehicle in a window 535, and the selected vehicle is shown in a window 510. The user may enter the user's play name at a text window 515 and is able to change the color of the selected vehicle by using a horizontal scroll bar 520.

"How it works" window 540 explains how a user can play a dice roll and how to win. For example, the user will receive a chance to roll a pair of dice at every 1,000 steps. Further, "How it Works" window 540 informs the duration of the challenge, a whole month of December, and rewards in a form of gift card or a completion badge.

UIs 600A-600C illustrates a current status of the user in the racecar gaming application. UI 600B is shown when the user scrolls down the UI 600A, and a UI 600C is shown when the user further scrolls down the UI 600A or scrolls down the UI of 600B. The UI 600A includes a current status window 610 showing a rank, laps, distance, and available rolls. The current status window 610 also includes a roll button 620, which the user pushes for rolling two virtual dice 650. A racetrack 630 is a track the user's vehicle is to run around and also shows locations of users' vehicles. Based on the laps or distance, the leaderboard 640 shows where the user is positioned with respect to other users. When a vehicle is clicked or selected by the user, an information window 660 pops up to show information of the selected vehicle. Further, such information is also shown in the leaderboard 640. For example, Clark T. is at 1.56 laps and Anony Mouse is at 0.00 laps.

By pressing or clicking the roll button 620, two dice are rolled showing two faces, and the available rolls is decreased by one. Based on the number of dots on the two faces of the dice, the vehicle advances on the racetrack 630. The available rolls may be calculated based on the number of application tokens. Based on the rank in the leaderboard 640, a performance score is given or calculated.

The card gaming application "CardSmart" is illustrated in UI 700A and 700B. The current number of steps and the daily goal are shown in the UIs 700A and 700B. Draw file 710 shows the current number of cards that the user can draw. The draw file 710 may show the remaining number of cards during a predetermined period for the challenge. For example, the predetermined period of challenge can be set to one week, and the remaining number of cards from yesterday is shown as being 36 in the draw file 710. When the predetermined period for the challenge is over, the remaining number of cards will become zero.

The goal of this card gaming application is to tap a box 720 to draw a number of cards and have the sum of those cards equal a target value 740 (e.g., 14 in this scenario). Here, the user may tap on the 7 card and on the other 7 card to create a sum of 14, which is the target value 740, thereby winning this round. The UI 700B shows an instance where the user tapped the first 7 card and a new card (i.e. the 5 card) appeared. To win this round, the user taps on the remaining 7 card to reach a total value of 14. When the user taps a card, the number of remaining cards in the draw file 710 is reduced by one. If the user wants more cards, the user needs to walk more steps to get more application tokens, at least until the maximum number of daily tokens is obtained. In this game, one application token may increase the remaining number of cards by 30, 40, or 50 or by a preset number. When the user wins one or more rounds, the number of wins will be added to the points, which will then be converted to a performance score.

The game of chance application "Jackpot!" is described with reference to UIs 800A and 800B in FIG. 8. A betting section 810 shows winning ratios based on a range of numbers selected by the user. If the user bets on an even number in the betting section 810 and taps on "+" to increase the number of coins for the game, the user will receive three times the coins the user bet when a roulette number turns out to be even in the roulette board 820.

The available plays may be added based on the remaining number of application tokens. In the UIs 800A and 800B, currently available plays are 40 and the goal is to reach 18,000 coins for the predetermined challenge period. When the user runs out of available plays, the user has to walk more to receive additional application tokens, at least until the daily maximum number of tokens is obtained. Here, one application token may allow the user to have, for example, 10, 20, or 30 plays for this game of chance. The performance score may be calculated based on the number of winning coins.

Another gaming application is called "Run, Set, Match!", as shown in UIs 900A-900C. The object of this gaming application is to generate various card runs or sets. My card section 910 shows a number of cards, from which a user can select a certain number of cards. The user is tasked with attempting to make a run or a set that optionally includes the dealer card. Rule section 920 informs how many points each set or run are worth or can generate. For example, a set of 6 can generate 160 points for the user, and a run of 4 can generate 60 points for the user.

Available plays indicate how many times the user can play. When the play button is pushed, the available plays are reduced by one, and the points are accumulated based on a set or run with user's selected cards from the card section 910A and the dealer card 360. The performance score of the user on this gaming application is calculated based on the point.

These gaming applications in FIGS. 4-9 are provided as examples, and other gaming applications, skill-learning applications, and social media applications may be added to the reward system 200 of FIG. 2. Other types of applications can also be added to the reward system 200 of FIG. 2, as persons having ordinary skill in the art can readily appreciate. From these various examples, a skilled person will recognize that these applications are generally non-physical in nature; instead, they rely on the user's wit, intelligence, or skill. The ability to win the exercise reward program can thus be based on non-physical achievements. The ability to engage with the applications so as to accrue points is based on a minimum level of exercise, which is designed to be achievable by substantially everybody. Thus, the ability to win the exercise reward program is primarily based on non-physical achievements and secondarily on physical achievements. Traditional exercise reward programs were primarily based on physical achievements, resulting in only very health individuals ever winning the reward. The disclosed embodiments effectively level the playing field by enabling all users to potentially win the reward program. In doing so, the embodiments provide improved techniques for incentivizing users to live healthy lifestyles.

Example Methods

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 10:
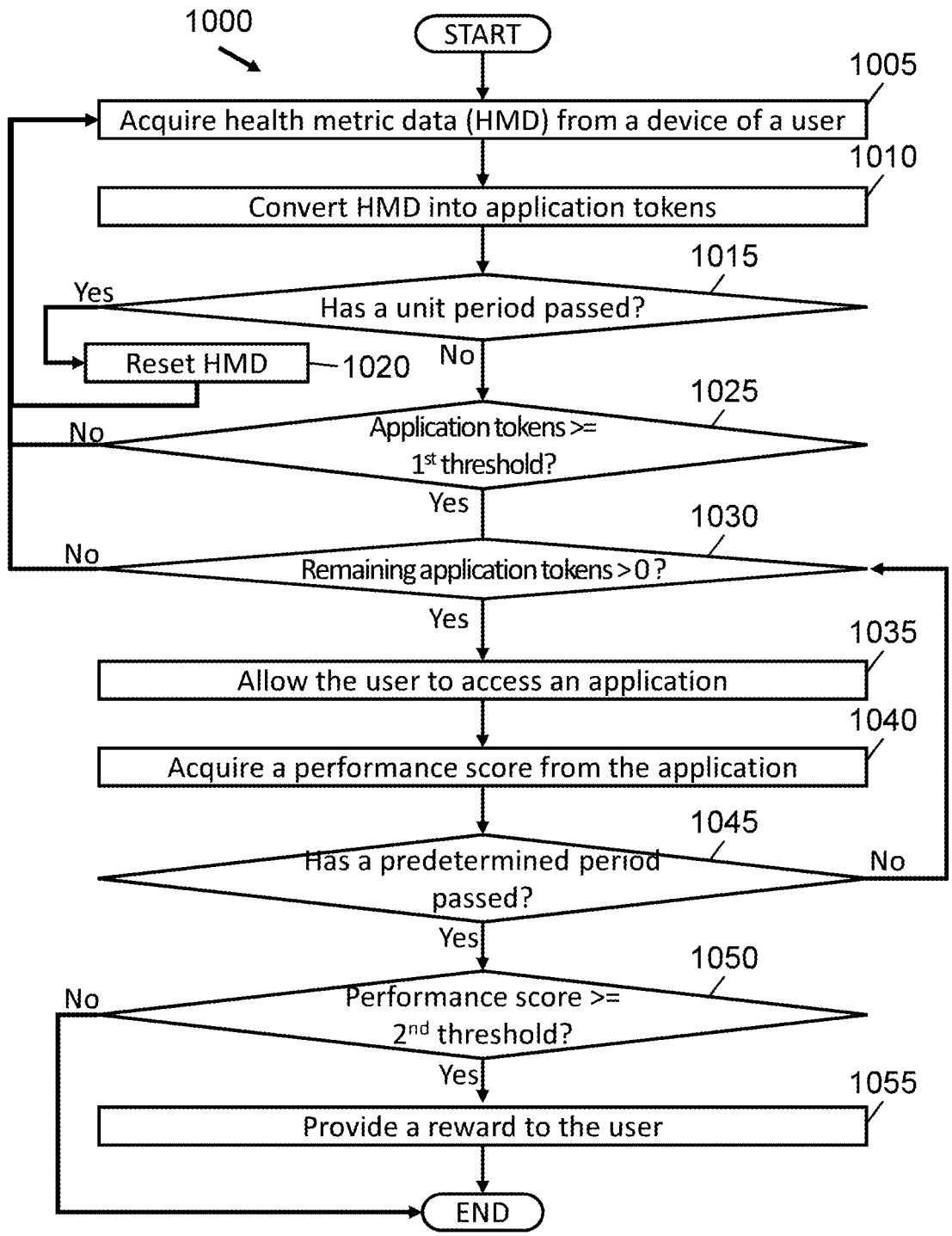
FIG. 10 illustrates a flowchart of a method for enabling users to play applications based on health metric data and to provide rewards based on a performance score achieved from playing the applications.

Attention will now be directed to FIG. 10, which illustrates a flowchart of a reward method 1000 based on a performance score that is accrued during engagement with one or more applications, where the ability to engage with those applications is based on a user's HMD. Reward method 1000 can be implemented within any of the systems or architectures mentioned herein, such as the reward system 100 of FIG. 1. Furthermore, the computing device 105 of FIG. 1 can be configured to implement the method 1000.

Stated another way, method 1000 describes various processes for providing access to a reward based on a user's performance in engaging with an application, where the user's access to engage with the application is determined based on the user's health metric data. As a consequence, the ability to obtain the reward is primarily based on the user's performance in engaging with the application and is not primarily based on the user's health metric data.

Health metric data (HMD) may be collected by one or more sensor devices, which include a pedometer, a smartphone, a pulsometer, a blood pressure monitor, a temperature sensor, a stroke tracker (e.g., a swim stroke measuring device), a GPS tracker, a blood glucose monitor, a camera, or any other physical or physiological sensor. Correspondingly, the HMD may include, but certainly is not limited to, the number of steps a user walks, the number of heartbeats of a user, the number of swim strokes of a user, the distance moved by a user (e.g., as determined by the GPS tracker), the number of spikes in the user's insulin levels or blood sugar levels, the amount of time the user spends outdoors, the amount of time the user spends working out at a gym, the amount of time engaged in an activity with another person, and so on. Any categorization or metric calculation among exercises, basic physiological signals, etc. can be used. When a user walks, runs, jogs, swims, or rides a bicycle, the HMD may further include a maximum heart rate and calories burned.

In step 1005, the HMD is acquired by a reward device (e.g., computing device 105 of FIG. 1) during a predetermined time period (e.g., perhaps a day or a unit period), where the HMD is received from the sensor devices (e.g., sensor device 160). The acquired HMD may be accumulated or tracked during a unit period (i.e. the predetermined time period), which can be a day, week, month, year, or any set period of time. For example, a number of steps are accumulated during the unit period, while the heart rate, body temperature, and blood pressure are tracked or monitored during the unit period.

The HMD is then converted to a number of application tokens in step 1010. This conversion step may be based on a linear increment or a non-linear increment. Further, there is a cap in the conversion step. For example, when 2,000 steps are to be converted into one application token, and the linear increment is used in the conversion step, 6,000 steps may be converted into three application tokens but no application tokens are converted after a step limit (e.g., 8,000 steps). Thus, 8,000 steps, 10,000 steps, and 20,000 steps are all converted into four application tokens. The above step limit is provided for explanation purposes only and may be set to other values. In this scenario, the number of application tokens, which each user is able to receive from walking, is also limited.

In one embodiment, users might be able to receive more application tokens after receiving the maximum application tokens that can be earned by achieving the baseline exercise requirement (e.g., perhaps from walking) during the unit period. For example, physiological data related to a healthy habit may be rewarded. That is, when the number of sleeping or resting hours is greater than or equal to some value (e.g., perhaps 6 or 8), the user may be rewarded a set number of additional application tokens. Likewise, users who follow a healthy living regimen can optionally be rewarded additional application tokens. In this way, most of the users are encouraged to follow healthy habits, while many rewarding programs reward only a small number of high performers, thereby discouraging the other users even before staring exercises.

In step 1015, it is determined whether or not the unit period has passed. When it is determined that the unit period has passed, the HMD is reset to zero in step 1020 and the reward method 1000 repeats step 1005 and the following steps.

In a case when it is determined that the unit period has not passed, it is further determined whether or not the number of application tokens or possibly the HMD are greater than a first threshold in step 1025. The first threshold may be predetermined based on a minimum or appropriate health related requirement that most users are able to reach during the unit period. Stated differently, the first threshold is predetermined based on a minimum health level that a majority of users are anticipated as being able to achieve.

For example, the first threshold may be a set number of tokens that can be acquired by performing a set amount of exercise or set amount of HMD. In another example, the first threshold may be a set amount of exercise or a set amount of HMD, which translates to a set number of tokens. In consideration of the above-described linear increment for walking in step 1010, the minimum requirement of walking may be set to 6,000 steps, and 3 tokens may be awarded to the user.

When it is determined that the number of application tokens or the amount of HMD are less than the first threshold, the reward method 1000 can go back to step 1005, where additional HMD can be acquired.

On the other hand, when it is determined that the number of application tokens or HMD is greater than or equal to the first threshold, it is also determined whether or not the remaining application tokens is greater than zero in step 1030. When it is determined that the number of remaining application tokens becomes zero, the reward method 1000 goes back to step 1005 so that the user may be able to accumulate additional HMD to receive additional application tokens, if additional tokens can still be earned during the unit period. If no additional tokens can be accrued during that time period, then the user's access to the application is limited.

When it is determined the number of remaining application tokens is greater than zero, the user is allowed to access applications based on the number of application tokens in step 1035. The user may be able to play gaming applications (e.g., a racecar game, a card game, a game of chance, a strategic game, a shooting game, and so on) by consuming application tokens, to use social media applications (e.g., Facebook®, Twitter®, Snapchat®, Instagram®, and so on) for a limited number of minutes per an application token, or to execute skill-learning applications (e.g., a word processor, a spreadsheet, a database, a programing language, and so on) by consuming the application tokens.

In an aspect, the application tokens may be designed to limit the duration a user is permitted to interact with an application. The application tokens may be designed to provide one or more gaming "lives" to a user while playing an application. The application tokens may be designed to grant or remove access to an application based on absence of the application tokens in the user's account. The application tokens may be designed to provide a certain amount of network bandwidth to a user, a certain amount of processor computing power or speed, or perhaps even an operating system priority level for an application. Indeed, the application tokens may be designed in any manner to restrict or limit a user's ability to interact with an application or perhaps even to restrict or limit the user's ability to interact with his/her smart device when the user does not have any application tokens. In this sense, the application tokens can be program-level constructs that operate to control features of applications.

The user's performance with the applications generates points, coins, or scores (i.e. the performance score mentioned previously) and are acquired from the applications in step 1040. Recall, the points are distinct relative to the application tokens.

In this step, performances are used to calculate a performance score by simply adding points/coins/scores from the applications or by adding points/coins/scores from the applications with corresponding weights. When groups are challenging each other, the performance of one group can be calculated by adding all individual user's performance scores in the same group. In an aspect, the application tokens are not compatible or interchangeable with the performance score.

After acquiring the performance score, it is determined whether or not a predetermined period has passed in step 1045. The predetermined period is predetermined for the exercise reward program and may not be equal to the unit period in step 1015. The predetermined period may be at least longer than or equal to the unit period but not shorter than the unit period.

When it is determined that the predetermined period has not passed, the reward method 1000 goes back to step 1030 so that the user is able to play applications for so long as the number of remaining application tokens is greater than zero.

When it is determined that the predetermined period has passed, it is also determined whether or not the performance score is greater than or equal to a second threshold in step 1050. The second threshold may be predetermined as the minimum score (e.g., performance score) to receive a reward in the exercise reward program. As such, when the performance score is determined to be greater than or equal to the second threshold, the user receives a reward in step 1055. On the other hand, users whose performance scores are less than the second threshold are not able to receive the reward because the predetermined period for the reward has passed.

Accordingly, the disclosed embodiments provide significant improvements and advantages over traditional exercise rewards programs. Whereas with traditional systems, only healthy individuals were incentivized to participate in an exercise rewards program, with the disclosed embodiments, all users are now incentivized to participate because all users have equal opportunities to potentially win the competition.

Example Computer Systems

Figure 11:
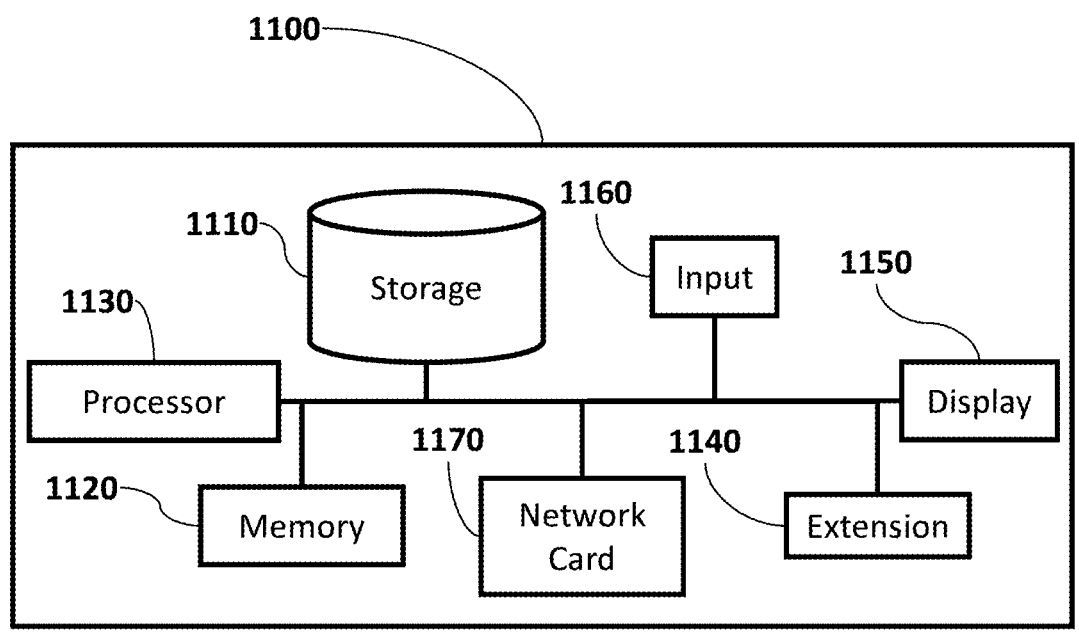
FIG. 11 illustrates a block diagram for a computing device.

Attention will now be directed to FIG. 11 which illustrates a computing device 1100 representative of the computing device 105 and the sensor device 160 of FIG. 1. The computing device 1100 may include, by way of non-limiting examples, server computers, desktop computers, laptop computers, notebook computers, sub-notebook computers, netbook computers, notepad computers, set-top computers, handheld computers, Internet appliances, mobile smartphones, tablet computers, personal digital assistants, video game consoles, embedded computers, smartwatches, smart sensors or any other devices capable of performing calculations/operations. Those of skill in the art will recognize that many smartphones are suitable for use in the system described herein. Suitable tablet computers include those with booklet, slate, and convertible configurations, known to those of skill in the art.

The computing device 1100 includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the computing device 1100 may include a storage 1110 (e.g., an example of a hardware storage device). The storage 1110 is one or more physical apparatus used to store data or programs on a temporary or permanent basis. In some embodiments, the storage 1110 may be volatile memory (e.g., memory 1120) and requires power to maintain stored information. In some embodiments, the storage 1110 may be non-volatile memory (e.g., memory 1120) and retains stored information when the computing device 1100 is not powered. In some embodiments, the non-volatile memory includes flash memory. In some embodiments, the non-volatile memory includes dynamic random-access memory (DRAM). In some embodiments, the non-volatile memory includes ferroelectric random-access memory (FRAM). In some embodiments, the non-volatile memory includes phase-change random access memory (PRAM). In some embodiments, the storage 1110 includes, by way of non-limiting examples, CD-ROMs, DVDs, flash memory devices, magnetic disk drives, magnetic tapes drives, optical disk drives, and cloud computing-based storage. In some embodiments, the storage 1110 may be a combination of devices such as those disclosed herein.

The storage 1110 includes executable instructions (i.e. code). The executable instructions represent instructions that are executable by the processor 1105 of the computing device 1100 to perform the disclosed operations, such as those described in the various methods. Furthermore, the storage 1110 excludes signals, carrier waves, and propagating signals. On the other hand, storage that carries computer-executable instructions may be "transmission media" and may include signals, carrier waves, and propagating signals. Thus, by way of example and not limitation, the current embodiments may include at least two distinctly different kinds of computer-readable media: computer storage media and transmission media.

The computing device 1100 further includes a processor 1130, an extension 1140, a display 1150, an input device 1160, and a network card 1170. The processor 1130 is a brain to the computing device 1100. The processor 1130 executes instructions which implement tasks or functions of programs. When a user executes a program, the processor 1130 reads the program stored in the storage 1110, loads the program on the RAM, and executes instructions prescribed by the program.

The processor 1130 may include, without limitation, Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware by performing the basic arithmetic, logical, control and input/output (I/O) operations specified by the instructions. As used herein, terms such as "executable module," "executable component," "component," "module," or "engine" may refer to the processor 1130 or to software objects, routines, or methods that may be executed by the processor 1130 of the computing device 1100. The different components, modules, engines, and services described herein may be implemented as objects or the processor 1130 that execute on the computing device 1100 (e.g., as separate threads).

In embodiments, the extension 1140 may include several ports, such as one or more universal serial buses (USBs), IEEE 1394 ports, parallel ports, and/or expansion slots such as peripheral component interconnect (PCI) and PCI express (PCIe). The extension 1140 is not limited to the list but may include other slots or ports that may be used for appropriate purposes. The extension 1140 may be used to install hardware or add additional functionalities to a computer that may facilitate the purposes of the computer. For example, a USB port may be used for adding additional storage to the computer and/or an IEEE 1394 may be used for receiving moving/still image data.

In some embodiments, the display 1150 may be a cathode ray tube (CRT), a liquid crystal display (LCD), or light emitting diode (LED). In some embodiments, the display 1150 may be a thin film transistor liquid crystal display (TFT-LCD). In some embodiments, the display 1150 may be an organic light emitting diode (OLED) display. In various some embodiments, the OLED display is a passive-matrix OLED (PMOLED) or active-matrix OLED (AMOLED) display. In some embodiments, the display 1150 may be a plasma display. In some embodiments, the display 1150 may be a video projector. In some embodiments, the display may be interactive (e.g., having a touch screen or a sensor such as a camera, a 3D sensor, a LiDAR, a radar, etc.) that may detect user interactions/gestures/responses and the like.

A user may input and/or modify data via the input device 1160 that may include a keyboard, a mouse, or any other device with which the use may input data. The display 1150 displays data on a screen of the display 1150. The display 1150 may be a touch screen so that the display 1150 may be used as an input device.

The network card 1170 is used to communicate with other computing devices, wirelessly or via a wired connection. Through the network card 1170, one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. The computing device 1100 may include one or more communication channels that are used to communicate with the network card 1170. Data or desired program codes are carried or transmitted in the form of computer-executable instructions or in the form of data structures vi the network card 1170.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, C#, Delphi, Fortran, Java, JavaScript, machine code, operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system that provides access to a reward based on a performance of a user in engaging with an application, where the user's access to engage with the application is determined based on health metric data of the user, such that an ability to obtain the reward is primarily based on the user's performance in engaging with the application and is not primarily based on the user's health metric data, the reward system comprising:
   one or more processors; and
   one or more hardware storage devices that store instructions that are executable by the one or more processors to cause the reward system to:
      acquire, during a determined time period, health metric data from a health tracking device, wherein the health metric data includes physical activity data and/or a physiological data;
      convert the health metric data into one or more application tokens;
      provide access to an application when a number of the one or more application tokens is greater than or equal to a first threshold;
      acquire, from the application, one or more points that are based on usage of the application; and
      facilitate access to a reward when the one or more points are greater than or equal to a second threshold.

2. The computer system of claim 1, wherein the health metric data includes at least one of: steps walked by the user, a distance that the user has run, swam, jogged, or cycled, or calories that the user has burned.

3. The computer system of claim 1, wherein the physiological data includes at least one of: a heart rate, a blood pressure, an oxygen saturation level in blood, a body temperature, a respiration rate, a number of sleeping hours, or a number of resting hours.

4. The computer system of claim 1, wherein the health tracking device is at least one of: a smartphone, a smartwatch, a pedometer, an oximeter, a pulsometer, a blood pressure monitor, or a temperature sensor.

5. The computer system of claim 1, wherein the one or more application tokens are distinct relative to the one or more points.

6. The computer system of claim 1, wherein the first threshold is predetermined based on a minimum health level that a majority of users, including said user, are anticipated as being able to achieve.

7. The computer system of claim 1, wherein the first threshold is individually adjusted based on a health level of each user who uses the reward system.

8. The computer system of claim 1, wherein the health metric data is reset after expiration of the determined time period.

9. The computer system of claim 1, wherein the health metric data is reset after expiration of the determined time period.

10. The computer system of claim 1, wherein the application is a middleware application between an operating system of the reward system and at least one of: a game application, a skill program, or a social media application.

11. A method for providing access to a reward based on a performance of a user in engaging with an application, where the user's access to engage with the application is determined based on health metric data of the user, such that an ability to obtain the reward is primarily based on the user's performance in engaging with the application and is not primarily based on the user's health metric data, the method comprising:
acquiring, during a determined time period, health metric data from a health tracking device, wherein the health metric data includes physical activity data and/or a physiological data;
converting the health metric data into one or more application tokens;
providing access to an application when a number of the one or more application tokens is greater than or equal to a first threshold;
acquiring, from the application, one or more points that are based on usage of the application; and
facilitating access to a reward when the one or more points are greater than or equal to a second threshold.

12. The method of claim 11, wherein the health metric data includes steps, a distance that the user has run, swum, jogged, or cycled, or calories that the user has burned.

13. The method of claim 11, wherein the health tracking device includes at least one of: a smartphone, a smartwatch, a pedometer, an oximeter, a pulsometer, a blood pressure monitor, or a temperature sensor.

14. The method of claim 11, wherein the one or more application tokens are different than the one or more points.

15. The method of claim 11, wherein the first threshold is predetermined based on a minimum health level that a majority of users, including said user, are anticipated as being able to achieve.

16. The method of claim 11, wherein the first threshold is adjusted based on a health level of the user.

17. The method of claim 11, wherein the health metric data is reset after expiration of the determined time period.

18. The method of claim 11, wherein the health metric data is reset after expiration of the determined time period.

19. The method of claim 11, wherein the application is a middleware application between an operating system and at least one of: a game application, a skill program, or a social media application.

20. One or more hardware storage devices that store instructions that are executable by one or more processors of a computer system to cause the computer system to:
acquire, during a determined time period, health metric data from a health tracking device, wherein the health metric data includes physical activity data and/or a physiological data;
convert the health metric data into one or more application tokens;
provide access to an application when a number of the one or more application tokens is greater than or equal to a first threshold;
acquire, from the application, one or more points that are based on usage of the application; and
facilitate access to a reward when the one or more points are greater than or equal to a second threshold.

* * * * *